United States Patent [19]

Mohler et al.

[11] 4,289,776
[45] Sep. 15, 1981

[54] XANTHINE DERIVATIVES

[75] Inventors: Werner Mohler, Hofheim; Manfred Jayme, Rüsselsheim; Jaromir Komarek, Wiesbaden, all of Fed. Rep. of Germany

[73] Assignee: Hoechst Aktiengesellschaft, Frankfurt am Main, Fed. Rep. of Germany

[21] Appl. No.: 32,536

[22] Filed: Apr. 23, 1979

Related U.S. Application Data

[63] Continuation of Ser. No. 775,551, Mar. 8, 1977, abandoned, which is a continuation-in-part of Ser. No. 531,048, Dec. 9, 1974, abandoned, which is a continuation-in-part of Ser. No. 479,434, Jun. 14, 1974, abandoned.

[30] Foreign Application Priority Data

Jun. 16, 1973 [DE] Fed. Rep. of Germany ....... 2330742

[51] Int. Cl.$^3$ ..................... A61K 31/52; C07D 473/06
[52] U.S. Cl. ....................................... 424/253; 544/271
[58] Field of Search ................. 544/271; 424/252, 253

[56] References Cited

U.S. PATENT DOCUMENTS 3,864,469  2/1975  Reiser et al. ........................ 424/252

Primary Examiner—Paul M. Coughlan, Jr.
Attorney, Agent, or Firm—Berman, Aisenberg & Platt

[57] ABSTRACT

Compounds of general formula

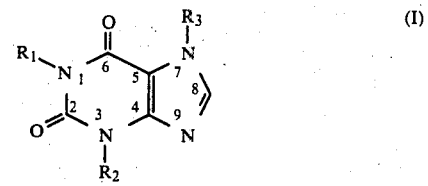

wherein one of the groups $R_1$ and $R_3$ is a straight-chain or branched oxoalkyl group consisting from 5 to 8 carbon atoms and the oxygen atom is attached to a non-terminal carbon atom and is separated from the nearest ring nitrogen atom by at least 3 carbon atoms in ($\omega$-1)-oxoalkyl groups and by at least 4 carbon atoms in oxoalkyl groups in which the oxygen atom is separated from the terminal carbon atom by more than one carbon atom, $R_2$ and the other one of groups $R_1$ and $R_3$ are straight chain or branched alkyl groups containing from 1 to 12 carbon atoms but wherein that group $R_1$ or $R_3$ which is other than an oxoalkyl group may also be hydrogen, one nitrogen-bound substituent being hydrogen or alkyl containing more than 1 carbon atom, and physiologically acceptable acid addition salts thereof, a process for their preparation and pharmaceutical compositions containing said compounds.

19 Claims, No Drawings

XANTHINE DERIVATIVES

This application is a continuation of application Ser. No. 775,551, filed Mar. 8, 1977, which is a continuation-in-part application of U.S. application Ser. No. 531,048, filed Dec. 9, 1974 which again is a continuation-in-part application of U.S. application Ser. No. 479,434, filed June 14, 1974, all now abandoned.

The invention relates to pharmaceuticals suitable for use in the treatment of diseases involving deficiencies in the blood vascular system. The pharmaceutical compositions contain certain oxoalkyl-(mono- or dialkyl)-xanthine derivatives having in particular vascular dilatory activity and good fibrinolytic action.

1-(Oxoalkyl)-3,7-dimethyl-xanthines and 7-(oxoalkyl)-1,3-dimethyl-xanthines have been prepared. These oxo compounds are readily soluble both in water and in lipoids and have a pronounced vascular dilatory action with a low toxicity.

Medicaments which contain, as active ingredient, xanthine derivatives substituted by identical or different alkyl groups with 1 to 6 carbon atoms: preferably 1 to 4 carbon atoms, in the 1-, 3- and 7-positions, at least one of which alkyl groups carries a hydrophilic group, preferably OH or COOH, are also already known. The number of hydrophilic groups per alkyl group is generally between 1 and the number of carbon atoms in the given alkyl group and the alkyl group which carries the hydrophilic group preferably contains 1 to 4 carbon atoms. (Compounds having a hydroxylsubstituent on a carbon atom adjacent to a ring nitrogen atom are unstable). The last-mentioned prior art does not disclose, however, that the hydrophilic group may be an oxoalkyl group, but such prior art disclosed only compounds in which the hydrophilising groups contain oxygen and have 2 or 3 carbon atoms and one hydrophilising group is in the β-position to the nearest ring nitrogen atom and all those alkyl groups which are not hydroxylated are methyl groups. Furthermore, the only compounds with only one hydrophylic group which have been specifically disclosed are derivatives of theobromine and of theophylline.

Pharmaceutical compositions are also known which contain as active ingredient, xanthines havin an oxoalkyl group with 6 to 20 carbon atoms in the 1- or 7-position and an alkyl group with 1 or 2 carbon atoms in the other of these two positions and in the 3-position. However no specific oxoalkyl compounds nor the preferred positions of the carbonyl group have been disclosed in the literature describing these compositions.

According to the present invention we now provide compounds of the formula

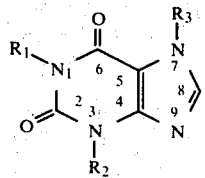

(I)

wherein one of the groups $R_1$ and $R_3$ is a straight-chain or branched oxoalkyl group containing from 5 to 8 carbon atoms and the oxygen atom is attached to a non-terminal carbon-atom and is separated from the nearest ring nitrogen atom by at least 3 carbon atoms in (ω-1)-oxoalkyl groups and by at least 4 carbon atoms in oxoalkyl groups in which the oxygen atom is separated from the terminal carbon atom by more than one carbon atom, $R_2$ and the other one of $R_1$ and $R_3$ are straight-chain or branched alkyl groups containing from 1 to 12 carbon atoms, but wherein that group $R_1$ or $R_3$ which is not oxoalkyl may also be hydrogen, one nitrogen-bound substituent being hydrogen or an alkyl group containing more than 1 carbon atom, and physiologically acceptable acid addition salts thereof. The oxoalkyl group is preferably straight-chained. The carbonyl group in the oxoalkyl group is preferably in the (ω-1)-position. At least one of the alkyl groups desirably contains more than 2 carbon atoms. Preferably $R_2$ is methyl.

In general the new compounds according to the invention have a vascular dilatory activity, a good fibrinolytic action and a low toxicity. Certain of the new compounds are soluble in lipoids. They additionally have the effect of improving the circulatory properties of blood and are therefore effective in the treatment of arterial blood flow disturbances. The pharmacological activity spectrum of the new compounds is otherwise substantially similar to that of the previously known oxoalkyl-dimethyl-xanthines (oxoalkyltheophyllines and oxoalkyl-theobromines).

The following are specific examples of the new compounds according to the invention:

1-Alkyl-3-methyl-7-(5-oxohexyl)-xanthines wherein the alkyl group is an ethyl propyl, n-butyl, isobutyl, pentyl, hexyl or decyl group, 1-(5-Oxohexyl)-3-methyl-7-alkyl-xanthines wherein the alkyl group is an ethyl, propyl, n-butyl, isobutyl, hexyl or decyl group, 1-(5-Oxohexyl)-3-butyl-7-propyl xanthine, 1-Alkyl-3-methyl-7-(5-oxoheptyl)-xanthines wherein the alkyl group is an ethyl, propyl, n-butyl, isobutyl, pentyl, hexyl or decyl group, 1-(5-Oxoheptyl)-3-methyl-7-alkyl-xanthines wherein the alkyl group is an ethyl, propyl, n-butyl, isobutyl, hexyl or decyl group, 1-(5-Oxoheptyl)-3-butyl-7-propyl xanthine, 1-Alkyl-3-methyl-7-(2-methyl-3-oxobutyl)-xanthines wherein the alkyl group is an ethyl, propyl, n-butyl, isobutyl, pentyl, hexyl or decyl group, 1-(2-Methyl-3-oxobutyl)-3-methyl-7-alkyl-xanthines wherein the alkyl group is an ethyl, propyl, n-butyl, isobutyl, hexyl or decyl group, 1-(2-Methyl-3-oxobutyl)-3-butyl-7-propyl-xanthine, 1-Alkyl-3-methyl-7-(6-oxoheptyl)-xanthines wherein the alkyl group is an ethyl, propyl, n-butyl, isobutyl, pentyl, hexyl or decyl group, 1-(6-Oxoheptyl)-3-methyl-7-alkyl-xanthines wherein the alkyl group is an ethyl, propyl, n-butyl, isobutyl, hexyl or decyl group, 3-Alkyl-7-(5-oxohexyl)-xanthines wherein the alkyl group is a methyl, ethyl, propyl, butyl, isobutyl, hexyl or decyl group. 3-(n-Butyl)-7-(ω-1)-oxoalkyl-xanthines wherein the oxoalkyl group is a 4-oxopentyl, 5-oxohexyl, 6-oxoheptyl or 7-oxooctyl group;

1-Methyl-3-butyl-7-(ω-1)-oxoalkyl-xanthines wherein the oxoalkyl group is a 4-oxopentyl, 5-oxohexyl, 6-oxoheptyl or 7-oxooctyl group.

The compounds of general formula I according to the invention may be prepared by the following processes, which processes constitute further features of the invention:

(a) Reaction of an appropriate 3-monoalkylxanthine or -1,3- or 3,7-dialkyl xanthine with a compound of formula

 (II)

(wherein R is an alkyl group containing from 1 to 4 carbon atoms, preferably a methyl or ethyl group) in an alkaline medium.

(b) Reaction of an alkali metal salt of an appropriate 3-monoalkylxanthine or 1,3- or 3,7-dialkyl-xanthine with a compound of formula

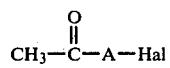 (III)

(wherein A is an alkylene group containing from 3 to 6 carbon atoms, which is preferably straight-chained and Hal is a halogen atom, preferably a chlorine or bromine atom) or with an acetal, ketal or thioketal therefrom and if necessary subsequently hydrolysing the product.

(c) Reaction of an alkali metal salt of an appropriate 1-oxoalkyl-3-alkyl-xanthine or 3-alkyl-7-oxoalkyl-xanthine with an appropriate alkyl halide or dialkyl sulphate in the presence of a solvent.

(d) For the preparation of compounds of general formula I as hereinbefore defined in which there are at least 3 carbon atoms between the carbonyl group and the nearest nitrogen atom (which means that the oxygen atom is separated by at least 4 carbon atoms from the nearest nitrogen atom)

Reaction of a compound of formula

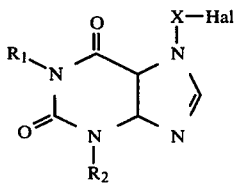 (IV)

or a compound of formula

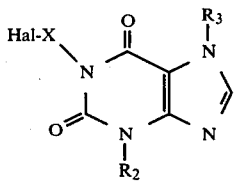 (V)

(wherein X is an alkylene group containing from 2 to 5 carbon atoms, which is preferably straight chained and Hal is a halogen atom, preferably a chlorine or bromine atom) with an alkali metal salt of an acetoacetate, preferably a sodium salt, and subsequently subjecting the reaction product to ketone splitting.

(e) Reaction of 3-alkylxanthine, in which the alkyl group has from 1 to 12 carbon atoms, or of a homologue of theobromine or theophylline having at least one methyl group replaced by an alkyl group containing at least 2 carbon atoms, preferably at least 3 carbon atoms, with a β-dialkylamino-alkyl methyl ketone (wherein the alkyl groups contain 1 to 2 carbon atoms and the alkylene group is branched and has 3 to 6 carbon atoms but only 2 carbon atoms in the main chain) in a solvent mixture comprising water and an organic solvent.

The reactions mentioned above are carried out in known manner, generally at temperatures of 50° to 150° C., preferably 60° to 120° C., optionally at elevated or reduced pressure but usually at atmospheric pressure. The various starting materials may be used in stoichiometric quantities or for economic reasons in nonstoichiometric quantities. In methods (b) and (c), the alkali metal salts are preferably prepared in situ. When reacting the straight chained ketone according to method (a), it is particularly advantageous to carry out the reaction in an organic amine such as pyridine because working up the reaction product is then considerably simplified. Otherwise, method (a) may advantageously be carried out in the presence of a strong alkali in a solvent mixture comprising water and an organic solvent. Ketone splitting in method (d) is carried out in the usual manner.

The organic solvents used are preferably those which are miscible with water, particularly monohydric alcohols, e.g. methanol, ethanol, propanol, isopropanol, the various butanols, also comprising ethylene glycol monomethyl ether and monoethyl ether, polyhydric alcohols such as ethylene glycol, aprotic solvents such as acetone, pyridine, formamide and dimethylformamide.

According to a still further feature of the invention there are provided pharmaceutical compositions comprising as active ingredient a compound of formula I as hereinbefore defined or a physiologically compatible acid addition salt thereof in association with a pharmaceutical carrier or excipient.

The pharmaceutical compositions according to the invention may be presented in a form suitable for oral, rectal or parenteral administration. They may be administered in solid form or in solution. Many of the xanthine derivatives according to the invention are sufficiently soluble in sterile water to be made up into injection solutions for parenteral administration.

Suitable forms for administration include for example solutions, emulsions, tablets, coated tablets, suppositories, capsules, granulates and sustained release forms. These may be prepared in known manner using the usual auxiliary agents such as excipients, disintegrants, binders, coating substances, swelling agents, lubricants, flavourings, sweeteners, substances to produce a sustained release effect and solubilising agents. Suitable auxiliary agents include for example lactose, mannitol, talcum, lactalbumin, starch, gelatin, cellulose and its derivatives such as methyl cellulose: hydroxyethyl cellulose and suitable swelling and non-swelling copolymers. Disintegration of the composition and hence also release of the active ingredient can be influenced by the addition of larger or smaller quantities of extending agents.

Advantageously the new compositions according to the invention are presented in the form of dosage units, each dosage unit being adapted to supply a fixed quantity of active ingredient, preferably 40 to 400 mg of active ingredient.

The compounds of the invention may be administered in an amount of e.g. 0.1 mg to 125 mg, preferably 1 mg to 50 mg per kg of body weight. The substances may be administered in a single dose or in a plurality of doses per day, if desired per infusionem.

If desired the new compositions may additionally contain a further active ingredient, for example a vitamin.

The following Examples serve to illustrate the preparation of the new compounds according to the invention

EXAMPLES

EXAMPLE 1

437.2 g of 3-methyl-7-propyl-xanthine suspended in a mixture of 240 g of methanol and 321 g of water are brought into solution by adding 160 g of 50% sodium hydroxide solution at elevated temperature. The mixture is heated to boiling and 358 g of 1-bromohexanone-(5) are then added. The mixture is heated under reflux for 4.5 hours. After cooling, the unreacted 3-methyl-7-propyl-xanthine is separated and the alcohol is distilled off. The aqueous solution is adjusted to pH 11 with sodium hydroxide solution and extracted with methylene chloride. 1-(5-Oxohexyl)-3-methyl-7-propyl-xanthine with a melting point of 69° to 70° C. is obtained in approximately 90% yield (based on reacted 3-methyl-7-propyl-xanthine) by recrystallising the residue of the methylene chloride solution from 5.2 liters of diisopropyl ether. The solubility of the product in water at 25° C. is about 3.2%. The solubility in ethanol and dimethyl sulphoxide is over 10%.

EXAMPLE 2

126 g of a colourless oil is obtained from 131 g of 3-methyl-7-n-hexyl-xanthine, 100 g of water, 60 g of methanol, 20 g of sodium hydroxide and 89.5 g of 1-bromohexanone-(5) analogously to Example 1. The oil is recrystallised by dissolving it in 60 ml of methanol and reprecipitating it from this methanolic solution with 1500 ml of diisopropyl ether. 1-(5-Oxohexyl)-3-methyl-7-n-hexyl-xanthine with a melting point of 50°–52° C. is obtained in 90% yield (based on reacted 3-methyl-7-n-hexyl-xanthine). The product is only sparingly soluble in water. The solubility in ethanol, dimethyl sulphoxide and dimethylformamide is over 10%.

EXAMPLE 3

86 g of a crude product is obtained from 92.1 g of 3-methyl-7-isobutyl-xanthine, 80 g of water, 48 g of methanol, 16 g of sodium hydroxide and 71.5 g of 1-bromohexanone-(5) analogously to Example 1. After vacuum distillation (196°–200° C./0.2 mm) and recrystallisation from diisopropyl ether, 1-(5-oxohexyl)-3-methyl7-isobutyl-xanthine with a melting point of 75°–76° C. is obtained in 90% yield. The solubility in ethanol, dimethyl sulphoxide and dimethylformamide is over 10%.

EXAMPLE 4

A suspension of 79.2 g of 3-methyl-7-(5-oxohexyl)-xanthine in a mixture of 120 g of water and 72 g of methanol is brought into solution by the addition of 18 g of sodium hydroxide at about 60° C. 55.5 g of n-propyl bromide are then added. After boiling under reflux for 24 hours, the reaction mixture is treated with 1 ml of concentrated sulphuric acid and cooled. Unreacted 3-methyl-7-(5-oxohexyl)-xanthine is filtered off and the alcohol is distilled off in vacuo. The remaining solution is made alkaline with 4 ml of 50% sodium hydroxide solution and extracted with 350 ml of methylene chloride. 1-n-Propyl-3-methyl-7-(5-oxohexyl)-xanthine with a melting point of 76°–78° C. is obtained in 85% yield from the residue of the methylene chloride solution by recrystallisation from isopropanol. The solubility of the product in ethanol, dimethyl sulphoxide and dimethylformamide is over 10%.

EXAMPLE 5

A crude product is obtained from 20.4 g of 3-methyl-7-ethyl-xanthine, 24 g of water, 24 g of methanol, 8 g of 50% sodium hydroxide solution and 17.9 g of 1-bromohexanone-(5) analogously to Example 1. After recrystallisation from a small quantity of methanol, 1-(5-oxohexyl)-3-methyl-7-ethyl-xanthine with a melting point of 102°–103° C. is obtained in almost quantitative yield. The solubility in water at 25° C. is about 2%. The solubility in ethanol and dimethyl sulphoxide is between 1 and 10% and in propylene glycol between 0.1 and 1%.

EXAMPLE 6

110 g of a yellow oil is obtained from 117 g of 3-methyl-7-(n-butyl)-xanthine, 140 g of water, 85 g of methanol, 20 g of sodium hydroxide and 95 g of 1-bromohexanone-(5) analogously to Example The oil is first distilled in vacuo (219° C./0.5 mm) and then crystallised from 700 ml of diisopropyl ether. 1-(5-Oxohexyl)-3-methyl-7-(n-butyl)-xanthine (melting point: 79° to 80° C.) is obtained in 60% yield.

Example 7

A mixture of 79.2 g of 3-methyl-7-(5-oxohexyl)-xanthine, 75 g of water, 75 g of methanol, 18 g of sodium hydroxide and 74.4 g of n-hexyl bromide is boiled under reflux for 4 days and then worked up in a manner analogous to Example 4. 82.9 g of a crude product are obtained from which I-(n-hexyl)-3-methyl-7-(5-oxohexyl)-xanthine is obtained in 90% yield after vacuum distillation (230°–232° C./0.3 mm). After recrystallisation from 500 ml of diisopropyl ether, the melting point is 35°–38° C.

Example 8

A mixture of 106 g of 3-methyl-7-(5-oxohexyl)-xanthine, 100 g of water, 100 g of methanol, 24 g of sodium hydroxide and 82 g of isobutyl bromide is boiled under reflux for 85 hours and then acidified with 5 ml of concentrated sulphuric acid. It is then boiled under reflux for a further 1.5 hours and then the unreacted 3-methyl-7-(5-oxohexyl)-xanthine (58.8 g) is removed by filtration. The crude product is worked up in a manner analogous to Example 4 to yield 57.7 g of a colourless residue from which 1-isobutyl-3-methyl-7-(5-oxohexyl)-xanthine with a melting point of 96°–97° C. is obtained in 95% yield (based on reacted 3-methyl-7-(5-oxohexyl)-xanthine) by recrystallisation from 1200 ml of diisopropyl ether.

Example 9

80.3 g of 3-methyl-7-n-decyl-xanthine, 140 g of water, 90 g of methanol, 10 g of sodium hydroxide and 44.6 g of 1-bromohexanone-(5) are boiled under reflux for 4 hours. After acidification with 2 ml of concentrated sulphuric acid, the reaction mixture is filtered hot to remove the unreacted 3-methyl-7-n-decyl-xanthine and the filtrate is worked up as in Example 1. 66.1 g of a crude crystalline product are obtained and are recrystallised from 500 ml of diisopropyl ether. The 1-(5- oxohexyl)-3-methyl-7-(n-decyl)-xanthine which is obtained in 85% yield melts at 64°–66° C.

Example 10

4.16 g (0.02 mol) of 3-n-butyl xanthine are added to a solution of 5.5 g of water, 4.4 g of methanol and 0.8 g (0.02 mol) of sodium hydroxide. The mixture is heated to 70° C. and stirred for one hour. 3.7 g (0.0206 mol) of 1-bromo-hexanone-(5) are added at 70° C. The solution is then stirred for 5 hours at 70° C. After cooling down to room temperature the crystals are isolated by suction, then washed with 20 ml of water and 20 ml of methanol and dried in the vacuum of the water jet pump at 70° to 100° C.

The yield is 4.4 g of a crude product (72% of the theory, referred to the butyl xanthine used) melting at 122° C.

4.3 g of the crude product are dissolved in 15 ml of water and 0.86 g of sodium hydroxide at 60° C.; 0.5 g of active carbon is added thereto, and the mixture is stirred for 15 minutes and then filtered. The filtrate is adjusted with sulphuric acid of 33% strength to pH 9.5 at 60° C., and the mixture is then cooled in an ice bath. The precipitated crystals were isolated by suction, washed with water until free from alkali and dried at 100° C. in the vacuum of a water jet pump.

The yield is 2.6 g (42.5% of the theory, referred to the 3-butyl-xanthine used). The product proves to be uniform on thin-layer chromatography and has a melting point of 134° C.

Example 11

166 g (1 mol) of 3-methyl-xanthine are introduced, while stirring into a mixture of 275 g of water, 220 g of methanol and 40 g (1 mol) of sodium hydroxide. The mixture is heated to 70° C. and stirred for about one hour. Then 183 g (1.02 mol) of 1-bromo-hexanone-(5) are dropped at this temperature into the mixture in the course of one hour. After about half an hour a thick pulp is formed which however can still be stirred and is stirred for a further 5 hours at 70° C. The pH-value does fall slightly and is in the range of from 5 to 7 at the end of the reaction. It is cooled to room temperature and the crystals are isolated by suction. These are dried at 70° to 100° C. in the vacuum of a water jet pump, after having been washed with 500 ml of water and 500 ml of methanol. 210 g of a crude product containing 73% of 3-methyl-7-(5-oxohexyl)-xanthine (=88% of the theory, referred to the reacted 3-methylxanthine) are obtained.

205 g of the crude product are dissolved at 60° C. in 1000 ml of water and 40 g of sodium hydroxide. 13 g of active carbon are added thereto; the mixture is then stirred for 15 minutes and filtered. The filtrate having a temperature of 60° C. is adjusted to pH 9.5 by adding 97 g of sulphuric acid (33% strength) over a period of one hour. The mixture is stirred for a further hour at 60° C. The precipitated crystals are isolated by suction, washed with water until they are free from alkali and dried in the vacuum of the water jet pump at 100° C.

The yield is 125 g of 3-methyl-7-(5-oxohexyl)-xanthine (=48% of the theory, referred to the 3-methylxanthine used). Having a melting point of 217° C.

A further 5% of this compound may be obtained from the mother lye by acidifying with additional sulphuric acid down to a pH-value of about 4 and subsequent purification.

After intraduodenal administration to narcotized cats the compound caused a significant and permanent increase in the cerebral blood circulation which is by several times superior to that similarly brought about by ethylene-diamine-theophylline. The compound is also much more compatible when administered intraperitoneally to mice. The $LD_{50}$-value for mice is in the range of from 1000 to 1500 mg/kg, while that of ethylene-diamine-theophylline is only 217 mg/kg.

Example 12

104.1 g of 3-(n-butyl)xanthine are added under stirring to a solution of 20.4 g of sodium hydroxide in 200 ml of water and 200 ml of methanol. Then at 70° C. 83.1 g of the ethylene ketal of 1-chloropentanone-(4) are dropwise added to the clear solution. After stirring for 41 hours at 70° C. the reaction mass is cooled to 20° C. and 34.5 g of the ethylene ketal of 3-(n-butyl)-7-(4'-oxopentyl)-xanthine are obtained. It has a melting point of 128° to 129° C. This ketal is heated to 70° C. for one hour in 1250 ml of 80% aqueous methanol in the presence of sulfuric acid and at a pH value of 1 to 2. After neutralisation and recrystallisation of the precipitate from alkaline solution wherein the pH value was changed from 13.5 to 10 26.8 g of 3-(n-butyl)-7-(4'-oxopentyl)-xanthine having a melting point of 140.5° to 141° C. are obtained (yield: 43.7%, referred to reacted xanthine).

Example 13

24.8 g of 3-(n-butyl)-7-(4'-oxopentyl)-xanthine are added to a solution of 3.5 g of sodium hydroxide in 80 ml of methanol and water (1:1). After stirring for 30 minutes at 40° C. 12.2 g of methyl iodide are added dropwise. After stirring for 50 hours the clear solution is concentrated under reduced pressure until dryness and the residue is diluted with ether and liberated from the starting material by addition of 1 N sodium hydroxide. After concentration of the neutralized ether solution and subsequent distillation at a temperature of the mixture of 130° C. under a pressure of 0.02 mm Hg 17.8 g of 1-methyl-3-(n-butyl)-7-(4'-oxopentyl)-xanthine having a melting point of 65° to 66° C. are obtained (yield: 84.2%, referred to the reacted starting xanthine).

Example 14

80.1 g of 3-(n-butyl)xanthine are added to a solution of 15.5 g of sodium hydroxide in 220 ml of a methanol/water mixture (1:1). After adding dropwise 53.7 g of 1-chlorohexanone-(5) to the clear solution which has a temperature of 70° C. the mixture is stirred at this temperature for 10 hours. After cooling to 20° C. and one recrystallisation of the precipitate from alkaline solution (wherein the pH value changes from 13.5 to 10), 34.4 g of pure 3-(n-butyl)-7-(5'-oxohexyl)-xanthine having a melting point of 141° C. are obtained (yield: 51.3%, referred to reacted 3-(n-butyl)xanthine).

Example 15

60 g of 3-n-butyl-7-(5'-oxohexyl)-xanthine are added to a solution of 8 g of sodium hydroxide in 160 ml of a methanol/water mixture (1:1). 28 g of methyl iodide are dropwise added to the clear solution having a temperature of 40° C. and the mixture is stirred at 48° C. for 24 hours. After concentration under reduced pressure the residue is diluted with 300 ml of diethylether and the unreacted 3-(n-butyl)-7-(5'-oxohexyl)-xanthine is removed by shaking with 1 N sodium hydroxide. After neutralisation, drying, concentration under reduced pressure and distillation at 140° C. temperature of the mixture and 0.02 mmHg 48.5 g of 1-methyl-3-(n-butyl)-7-(5'-oxohexyl)-xanthine are obtained from the ether phase as a viscous oil ($n_D^{20}=1.5320$; yield 77.2%, referred to reacted starting xanthine). Analysis: $C_{16}H_{24}N_4O_3 = 320.396$

|  | C | H | N |
|---|---|---|---|
| calculated: | 59.98% | 7.55% | 17.49% |
| found: | 60.05% | 7.74% | 17.36% |

Examles 16 to 19

In the same way as under example 15 the following compounds were prepared.

16. 3-(N-Butyl)-7-(6'-oxoheptyl)xanthine, melting point 110° to 111° C., from 3-(n-butyl)xanthine and 1-chloroheptanone-(6) at 70° C. temperature of the mixture and under stirring for 43 hours (yield 80.8%, referred to reacted 3-butylxanthine).

17. 3-(n-Butyl)-7-(7'-oxooctyl)-xanthine, melting point 98.5° to 99° C., from 3-(n-butyl)xanthine and 1-bromooctanone-(7) at a mixture temperature of 70° C. under stirring for 39 hours (yield: 52.2%, referred to reacted 3-butylxanthine).

18. The reaction is performed according to example 15 from 3-(n-butyl)-7-(6'-oxoheptyl)-xanthine and methyl iodide, but at a temperature of the mixture of 50° C. under stirring for 46 hours. Prior to the distillation at a bath temperature of 140° C. and 0.02 mmHg the product is purified by column chromatography at silica gel 60 (Merck) with methylene chloride/acetone (80:2) as eluent. 1-Methyl-3-(n-butyl)-7-(6'-oxoheptyl)-xanthine was obtained as a viscous oil ($n_D^{20}$ 1.5280; yield 80.1%, referred to reacted 3-(n-butyl)-7-(6'-oxoheptyl)-xanthine.

Analysis: $C_{17}H_{26}N_4O_3 = 334.423$

|  | C | H | N |
|---|---|---|---|
| calculated: | 61.06% | 7.84% | 16.75% |
| found: | 60.85% | 7.87% | 16.59% |

19. 1-Methyl-3-(n-butyl)-7-(7'-oxooctyl)-xanthine from 3-(n-butyl)-7-(7'-oxooctyl)-xanthine and methyl iodide at a temperature of the mixture of 50° C. under stirring for 46 hours. The product is obtained in colorless crytals, melting point 52° C. (yield: 94.4%, referred to reacted 3-(n-butyl)-7-(7'-oxooctyl)-xanthine.

Example 20

40.4 g of 3-(n-Butyl)-7-n-pentylxanthine, 17.8 g of methylvinylketone and 7.3 ml of triethylamine are refluxed under stirring for 7 hours. After concentration under reduced pressure the residue is diluted with 200 ml of diethylether and extracted at repeated times with 1 N sodium hydroxide. The ether phase was washed to neutrality, dried and concentrated to dryness under reduced pressure. After one rerystallisation from petrolether (boiling range from 60° to 90° C.) under addition of active charcoal 25.6 g of 3-(n-butyl)-7-(n-pentyl)-1-(3'-oxobutyl)-xanthine having a melting point of 65° C. are obtained (yield 71.7%, referred to the reacted starting xanthine).

Analysis: $C_{18}H_{28}N_4O_3 = 348.45$

|  | C | H | N |
|---|---|---|---|
| calculated: | 62.05% | 8.10% | 16.08% |
| found: | 62.09% | 8.23% | 15.87% |

PHARMACOLOGICAL EXPERIMENTS

Animal tests were carried out with various oxoalkylxanthine derivatives, in which the toxicity in the mouse, the increase of cerebral and muscular blood perfusion at the cat and the fibrinolytic effect in vitro in the Hanging-Clot-test were measured. Furthermore the broncholytic effect of various compounds was tested. The results were compared with those obtained with the known substance 1-(5-oxohexyl)-3,7-dimethylxanthine which was known to have a vaso-dilatory effect with a low toxicity (cf. U.S. Pat. No. 3,737,433).

The tested compounds are evident from the following Table 1.

TABLE 1

| Sample No. | substances | melting point °C. |
|---|---|---|
| 1 | 1-Propyl-3-methyl-7-oxohexylxanthine | 76–78 |
| 2 | 1-Isobutyl-3-methyl-7-oxohexylxanthine | 96–97 |
| 3 | 1-Hexyl-3-methyl-7-oxohexylxanthine | 35–38 |
| 4 | 1-Oxohexyl-3-methyl-7-propylxanthine | 69–70 |
| 5 | 1-Oxohexyl-3-methyl-7-n-butylxanthine | 79–80 |
| 6 | 1-Oxohexyl-3-methyl-7-decylxanthine | 64–66 |
| 7 | 1-Oxohexyl-3-methyl-7-ethylxanthine | 102–103 |
| 8 (comparison) | 1-(5-Oxohexyl)-3,7-dimethylxanthine | 102–105 |

PHARMACOLOGICAL TESTS

1. Cerebral and muscular blood perfusion by fluvography

These tests were performed at the cat according to K. Popendiker, I. Boksay and V. Bollmann ("Arzneimittel Forschung" vol. 21 (1971), page 1160).

2. Broncholytic effect at the narcotized guinea-pig

This test was performed according to H. Konsett and R. Rössler ("Archiv exp. Path. Pharmak." vol. 195 (1940), page 71).

3. Broncholytic effect at the isolated trancheal chain

This test was performed according to J. C. Castillo and E. J. de Beer ("J. Pharm. Ther." vol. 90 (1947), page 104).

4. Fibrinolytic effect

This effect was measured by the Hanging-Clot-test according to K. N. von Kaulla ("Journ. med. Chem." vol. 8 (1965), page 164) in using human blood. The incubation time was 24 or 48 hours.

5. Toxicity in the mouse

The toxicity was determined as $LD_{50}$—range or as $LD_{50}$ according to Litchfield and Wilcoxon ("J. Pharmacol. exp. Ther." 97 (1949), page 399) in the mouse.

TESTS RESULTS

The values obtained in the mentioned test 1 are given as $\Delta\lambda$ and as half-life values in Table 2 and the results of tests 2 to 5 are enumerated in Table 3. In Table 2 $\Delta\lambda$ is the change of blood perfusion.

TABLE 2

| Sample No. | Dose mg/kg i.v. | Cerebral blood perfusion Δλ | Cerebral blood perfusion half-life min. | Muscular blood perfusion Δλ | Muscular blood perfusion half-life min. | Animals n |
|---|---|---|---|---|---|---|
| 2 | 1 | +1.85 | 1.0 | 0 | — | 2 |
|   | 5 | +3.45 | 14.3 | +0.05 | 0.60 | 2 |
| 3 | 1 | +0.97 | 0.4 | −0.05 | 3.30 | 3 |
|   | 2 | +1.45 | 7.0 | 0 | — | 2 |
| 4 | 1 | +4.33 | 4.0 | +0.13 | 3.70 | 3 |
|   | 2 | +6.33 | 5.8 | +0.07 | 0.80 | 3 |
|   | 5 | +13.00 | 14.7 | +0.08 | 3.70 | 3 |
| 5 | 1 | +2.50 | 1.3 | 0 | — | 2 |
|   | 2 | +2.55 | 1.3 | 0 | — | 2 |
|   | 5 | +2.40 | 3.0 | 0 | — | 2 |
| 6 | 1 | +1.40 | 0.2 | 0 | — | 1 |
|   | 3 | +2.8 | 0.5 | +0.30 | 4.00 | 1 |
| 7 | 1 | +2.46 | 1.5 | +0.22 | 0.40 | 5 |
|   | 2 | +5.17 | 5.0 | +0.10 | 5.00 | 3 |
|   | 5 | +8.07 | 8.2 | +0.20 | 0.50 | 3 (1)(+) |
| 8 | 1 | +0.44 | 0.9 | +0.02 | 1.10 | 13 (10) |
|   | 5 | +0.86 | 2.4 | +0.03 | 3.30 | 40 (23) |
|   | 10 | +1.15 | 8.6 | +0.15 | 2.80 | 33 (15) |
|   | 20 | — | — | +1.38 | >15 | (2) |

TABLE 3

| Sample No. | Toxicity mg/kg i.p. | Dose mg/kg i.v. | Change of the bronchospasm in % 2 min. i.p. against acetylcholine | histamine | acrotonine | n | Inhibition of isoprenaline reaction in % concentration $3 \times 10^{-6}$ | $10^{-5}$ | $3 \times 10^{-5}$ | $10^{-4}$ | n | Fibrinolytic effect Hanging-Clot-Test Minimum Concentration mMol for beginning lysis | partial lysis | complete lysis |
|---|---|---|---|---|---|---|---|---|---|---|---|---|---|---|
| 1 | 100–250 | 3(2) | −33 | −63 | −40 | each 1 | | | | | | — | 40 | (20)(3) |
|   |   | 10(2) | −55 | −73 | −82(1) | | | | | | | | | |
| 2 | 250–500 | 3 | — | −80 | −20 | each 1 | | | | | | — | — | — |
|   |   | 10 | −29 | −73 | −47 | | | | | | | | | |
| 3 | 250–500 | 3 | −23 | −52 | −50 | each 1 | | | | | | — | — | — |
|   |   | 10 | −85 | −90 | −100 | | | | | | | | | |
| 4 | 107 i.v. | 3 | −40 | −75 | −83 | each 2 | 2 | 20 | 94 | 100 | each 2 | — | — | 50(25)(3) |
|   | 860 per os | 10 | −75 | −86 | −93 | | | | | | | | | |
| 5 | 250–500 | 5 | −100 | −42 | −70 | each 1 | | | | | | — | — | — |
|   |   | 10 | −100 | −69 | −100 | | | | | | | | | |
| 6 | 500 | 10(2) | −50 | −40 | −50 | each 1 | | | | | | — | — | — |
| 7 | 250–500 | 3 | −28 | −47 | −42 | each 2 | | | | | | — | 50(25)(3) | — |
|   |   | 10 | −96 | −90 | −81 | | | | | | | | | |
| 8 (Comparison) | — | 3 | −15 | −4 | — | 2,2,- | 0 | 5 | 30 | 89 | 7,20, 17,18 | — | 100(50)(3) | |
|   |   | 5 | — | −94 | — | -3,- | | | | | | | | |
|   |   | 10 | −41 | −83 | — | 3,5,- | | | | | | | | |
|   |   | 20 | −72 | −100 | — | 1,2,- | | | | | | | | |

(1) Longtime effect
(2) Sample in propanediol
(3) Bracket = 48 hours

DISCUSSION OF THE RESULTS

As it is evident from the above Tables sample number 2 shows a stronger and longer cerebral blood perfusion. Thus, a dose of 5 mg/kg has an effect which is about four times stronger and its half-life is more than five times longer than those of the comparison sample. In the dose of 2 mg/kg of sample 3 its effect is about two times as strong and its half-life is about three times as long as the corresponding effects of comparison sample number 8, however with the higher dose of 5 mg/kg. In all dose values of sample number 4 an essentially stronger (more than 10 times) and longer cerebral blood perfusion and a stronger muscular blood perfusion, compared with the values of the corresponding dosages of comparison sample number 8 is obtained. Sample number 5 effects an increase of the cerebral blood perfusion over the comparison sample which at a dose of 1 mg/kg is nearly six times higher and at a dose of 5 mg/kg is about three times higher than that of the comparison sample. An improvement over the comparison sample is also shown by sample number 7 wherein the cerebral blood perfusion at the dose of 1 mg/kg is about five times higher and at the dose of 5 mg/kg is about nine times higher than that of sample number 8. The half-life is 1.5 times longer at a dose of 1 mg/kg and more than three times longer at a dose of 5 mg/kg compared with that of sample number 8. Besides that it is also evident from Table 2 that samples 1, 4 and 7 have an improved fibrinolytic effect which is two times as strong as that of comparison sample number 8. Furthermore the broncholytic effect against acetylcholine of samples 3 to 5 and 7 is better than the corresponding effect of sample 8 and additionally samples number 3, 4 and 7 have also an improved broncholytic effect against histamine, compared with sample number 8.

It is not intended that the examples given herein should be construed to limit the invention thereto, but rather they are submitted to illustrate some of the specific embodiments of the invention. Resort may be had to various modifications and variations of the present invention without departing from the spirit of the discovery or the scope of the appended claims.

What we claim is:

1. A compound of the formula

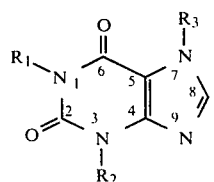

wherein one of $R_1$ and $R_2$ is a straight-chain or branched oxoalkyl having from 5 to 8 carbon atoms; the oxygen atom of the oxoalkyl is attached to a non-terminal carbon atom, is separated from the nearest ring nitrogen atom by at least three carbon atoms when it is in the (ω-1)-position of the oxoalkyl and is separated from the nearest ring nitrogen atom by at least four carbon atoms when it is in a position other than the (ω-1)-position of the oxoalkyl;

$R_2$ is alkyl having up to 12 carbon atoms and the other of $R_1$ and $R_3$ is straight-chain or branched alkyl having from 1 to 12 carbon atoms; at least one of $R_1$, $R_2$ and $R_3$ being alkyl having more than one carbon atom.

2. A compound according to claim 1 wherein the oxoalkyl has a carbonyl in the (ω-1)-position.

3. A compound according to claim 1 wherein the oxoalkyl is straight-chain oxoalkyl.

4. A compound according to claim 1 wherein at least one of $R_1$ and $R_3$ is alkyl having more than two carbon atoms and $R_2$ is methyl.

5. A member according to claim 1 wherein $R_2$ is methyl.

6. A compound according to claim 1 wherein at least one of $R_1$, $R_2$ and $R_3$ is alkyl having more than two carbon atoms.

7. A 1-alkyl-3-methyl-7-(5-oxohexyl)-xanthine according to claim 1 wherein the alkyl is a straight-chain or branched member selected from the group consisting of propyl, n-butyl, isobutyl, n-hexyl, isohexyl, n-decyl and isodecyl.

8. A 1-(5-oxohexyl)-3-methyl-7-alkylxanthine according to claim 1 wherein the alkyl is a straight-chain or branched member selected from the group consisting of propyl, n-butyl, isobutyl, n-hexyl, isohexyl, n-decyl and isodecyl.

9. The compound according to claim 7 which is 1-(n-propyl)-3-methyl-7-(5-oxohexyl)-xanthine.

10. A compound according to claim 8 wherein the member is propyl.

11. A pharmaceutical composition comprising a pharmaceutical carrier or excipient and a member according to claim 1 in an amount and concentration which are effective to improve blood circulation of an arterial-blood-flow-deficient host to which the composition is administered.

12. A pharamceutical composition in dosage-unit form comprising active ingredient in association with a pharmaceutical carrier or excipient, the active ingredient comprising a compound as defined in claim 1 in an amount and concentration which are effective to improve blood circulation of a person having an arterial-blood-flow deficiency and to whom the composition is administered.

13. A pharmaceutically-acceptable and therapeutically useful injectable solution in sterile water containing from 10 to 400 mg per unit dose of a compound as defined in claim 1.

14. A composition according to claim 12 wherein each dosage unit contains from 10 to 400 mg of the active ingredient.

15. A process for treating a person suffering from an arterial bloodflow disturbance or vascular dilatory insufficiency which comprises administering to such person an effective amount of a compound according to claim 1 in the form of a pharmaceutical composition.

16. A process according to claim 15 wherein the pharmaceutical composition contains from 0.1 to 125 milligrams, per kilogram of body weight of the person, of said compound.

17. A process according to claim 15 for treating a person suffering from an arterial blood-flow disturbance.

18. A process according to claim 15 for treating a person suffering from a vascular dilatory insufficiency.

19. A process according to claim 15 for treating a person suffering a fibrinolytic-system disturbance.

* * * * *